United States Patent
Baeumner et al.

(10) Patent No.: US 6,576,460 B1
(45) Date of Patent: Jun. 10, 2003

(54) FILTRATION-DETECTION DEVICE AND METHOD OF USE

(75) Inventors: Antje J. Baeumner, Ithaca, NY (US); Richard A. Montagna, Grand Island, NY (US)

(73) Assignees: Cornell Research Foundation, Inc., Ithaca, NY (US); Innovative Biotechnologies International, Inc., Grand Island, NY (US)

( * ) Notice: Subject to any disclaimer, the term of this patent is extended or adjusted under 35 U.S.C. 154(b) by 87 days.

(21) Appl. No.: 09/698,564

(22) Filed: Oct. 27, 2000

Related U.S. Application Data

(60) Provisional application No. 60/162,371, filed on Oct. 28, 1999.

(51) Int. Cl.[7] ............. G01N 33/53; G01N 33/543; G01N 33/558

(52) U.S. Cl. ............ 435/287.1; 435/287.2; 435/287.9; 435/288.5; 435/288.6; 435/288.7; 435/808; 435/814; 435/817; 435/822; 422/55; 422/57; 422/58; 422/68.1; 422/76; 422/77; 422/82.01; 422/82.11; 422/90; 422/97; 422/98; 422/101; 422/119; 422/255; 422/939; 436/149; 436/164; 436/518; 436/528; 436/541; 436/805; 436/806; 436/823; 436/824; 204/193; 204/194; 204/400; 204/409; 204/411; 204/422; 204/435; 204/228.1; 204/660; 204/665; 204/672; 210/348; 210/500.1; 210/506; 210/634; 210/638; 210/645; 210/660; 210/679; 210/690; 210/767; 210/902; 210/908

(58) Field of Search ............... 210/348, 500.1, 210/500.21, 500.27, 500.29, 502.1, 506, 634, 638, 644, 645, 649–651, 653, 655, 660, 679, 690, 767, 902, 908; 422/55, 57, 58, 68.1, 76, 77, 82.01–82.09, 82.11, 90, 91, 98, 101, 119, 255, 939; 435/287.1, 287.2, 287.9, 288.5, 288.6–288.7, 808, 814, 817, 822; 436/149–151, 164, 169, 172, 177, 178, 518, 528, 529, 530, 532, 535, 536, 538, 541, 805, 806, 823, 824; 204/193, 194, 400, 406, 403, 407, 409–412, 415, 418, 419, 422, 424, 426, 435, 228.1, 229.6, 229.4, 229.8, 230.2, 298.03, 298.32, 660, 665, 672

(56) References Cited

U.S. PATENT DOCUMENTS

| | | | |
|---|---|---|---|
| 4,048,298 | A | 9/1977 | Niswender |
| 4,172,770 | A | 10/1979 | Semersky et al. |
| 4,225,410 | A | * 9/1980 | Pace .................... 204/406 |

(List continued on next page.)

FOREIGN PATENT DOCUMENTS

| EP | 0 276 165 | 7/1988 |
|---|---|---|
| EP | 0 387 696 A2 | 9/1990 |
| EP | 0 402 917 B1 | 12/1990 |
| EP | 0 437 092 A1 | 7/1991 |

(List continued on next page.)

OTHER PUBLICATIONS

Durst, "Automated Analyzer for the Determination of Potassium and Sodium in Whole Blood," *Clinica Chimica Acta*, 80:225–234 (1977).

Durst et al., "Organic Electrochemical Techniques Having Potential Clinical Application," *Clinical Chemistry*, 28:1922–1930 (1982).

(List continued on next page.)

*Primary Examiner*—Long V. Le
*Assistant Examiner*—Kartic Padmanabhan
(74) *Attorney, Agent, or Firm*—Nixon Peabody LLP

(57) ABSTRACT

The present invention relates to a filtration-detection device for detecting or quantifying an analyte in a test sample including a filtration device having a first binding material immobilized thereto, wherein the first binding material is capable of binding to a portion of the analyte, and a detection assembly positioned relative to the filtration device to detect or quantify analyte bound to the first binding material. The present invention also relates to methods of using the filtration-detection device.

15 Claims, 9 Drawing Sheets

U.S. PATENT DOCUMENTS

| | | | |
|---|---|---|---|
| 4,235,601 A | | 11/1980 | Deutsch et al. |
| 4,517,288 A | | 5/1985 | Giegel et al. |
| 4,517,303 A | | 5/1985 | Freytag et al. |
| 4,571,543 A | * | 2/1986 | Raymond et al. ........... 257/414 |
| 4,594,327 A | | 6/1986 | Zuk |
| 4,605,630 A | | 8/1986 | Kung et al. |
| 4,636,479 A | | 1/1987 | Martin et al. |
| 4,668,619 A | | 5/1987 | Greenquist et al. |
| 4,695,554 A | | 9/1987 | O'Connell et al. |
| 4,703,017 A | | 10/1987 | Campbell et al. |
| 4,708,933 A | | 11/1987 | Huang et al. |
| 4,752,572 A | | 6/1988 | Sundberg et al. |
| 4,806,311 A | | 2/1989 | Greenquist |
| 4,822,566 A | | 4/1989 | Newman |
| 4,855,240 A | | 8/1989 | Rosenstein et al. |
| 4,874,710 A | | 10/1989 | Piran |
| 4,916,080 A | | 4/1990 | Imai et al. |
| 4,920,046 A | | 4/1990 | McFarland et al. |
| 4,939,098 A | | 7/1990 | Suzuki et al. |
| 5,001,048 A | | 3/1991 | Taylor et al. |
| 5,006,473 A | | 4/1991 | Bouma et al. |
| 5,045,285 A | | 9/1991 | Kolesar, Jr. |
| 5,047,245 A | | 9/1991 | Bally et al. |
| 5,081,013 A | | 1/1992 | Rovelli et al. |
| 5,085,987 A | | 2/1992 | Olson |
| 5,089,181 A | | 2/1992 | Hauser |
| 5,096,629 A | | 3/1992 | Nanba et al. |
| 5,130,257 A | | 7/1992 | Baer et al. |
| 5,141,751 A | | 8/1992 | Tomikawa et al. |
| 5,141,868 A | | 8/1992 | Shanks et al. |
| 5,155,022 A | | 10/1992 | Naqui et al. |
| 5,169,789 A | | 12/1992 | Bernstein |
| 5,173,406 A | | 12/1992 | Hosoda et al. |
| 5,194,133 A | * | 3/1993 | Clark et al. ................. 204/403 |
| 5,198,367 A | | 3/1993 | Aizawa et al. |
| 5,200,051 A | | 4/1993 | Cozzette et al. |
| 5,208,143 A | | 5/1993 | Henderson et al. |
| 5,248,590 A | | 9/1993 | Rutner et al. |
| 5,308,775 A | | 5/1994 | Donovan et al. |
| 5,310,650 A | | 5/1994 | McMahon et al. |
| 5,312,762 A | | 5/1994 | Guiseppi-Elie |
| 5,340,716 A | | 8/1994 | Ullman et al. |
| 5,346,832 A | | 9/1994 | Aizawa et al. |
| 5,354,692 A | | 10/1994 | Yang et al. |
| 5,369,036 A | | 11/1994 | Mercolino et al. |
| 5,384,264 A | | 1/1995 | Chen et al. |
| 5,389,523 A | | 2/1995 | Plant et al. |
| 5,393,527 A | | 2/1995 | Malick et al. |
| 5,399,500 A | | 3/1995 | Oppenheimer et al. |
| 5,416,214 A | | 5/1995 | Pease et al. |
| 5,459,041 A | | 10/1995 | Blaser et al. |
| 5,491,097 A | * | 2/1996 | Ribi et al. ............... 422/82.01 |
| 5,494,803 A | | 2/1996 | Carbonell et al. |
| 5,516,638 A | | 5/1996 | Urnovitz et al. |
| 5,532,133 A | | 7/1996 | Barnwell |
| 5,567,591 A | | 10/1996 | Lovell et al. |
| 5,591,645 A | | 1/1997 | Rosenstein |
| 5,635,357 A | | 6/1997 | Malick et al. |
| 5,665,552 A | | 9/1997 | Maret et al. |
| 5,670,328 A | | 9/1997 | Inoue et al. |
| 5,672,478 A | | 9/1997 | Singh et al. |
| 5,712,170 A | | 1/1998 | Kouvonen et al. |
| 5,738,868 A | | 4/1998 | Shinkarenko |
| 5,753,519 A | | 5/1998 | Durst et al. |
| 5,756,362 A | | 5/1998 | Durst et al. |
| 5,756,879 A | * | 5/1998 | Yamagishi et al. ......... 204/424 |
| 5,766,961 A | | 6/1998 | Pawlak et al. |
| 5,769,080 A | | 6/1998 | Unger et al. |
| 5,770,460 A | | 6/1998 | Pawlak et al. |
| 5,776,487 A | | 7/1998 | Maxfield Wilson et al. |
| 5,780,010 A | | 7/1998 | Lanza et al. |
| 5,789,154 A | | 8/1998 | Durst et al. |
| 5,817,334 A | | 10/1998 | Schmidt et al. |
| 5,958,791 A | | 9/1999 | Roberts et al. |
| 6,004,442 A | * | 12/1999 | Choulga et al. ............ 204/415 |
| 6,040,195 A | * | 3/2000 | Carroll et al. ................ 422/55 |
| 6,086,748 A | | 7/2000 | Durst et al. |
| 6,103,127 A | * | 8/2000 | Pourfarzaneh ............. 210/690 |
| 6,159,745 A | | 12/2000 | Roberts et al. |
| 6,248,596 B1 | | 6/2001 | Durst et al. |
| 6,358,752 B1 | * | 3/2002 | Durst et al. ................. 204/194 |
| 6,395,517 B1 | * | 5/2002 | Abbaszadegan et al. ....... 435/6 |

FOREIGN PATENT DOCUMENTS

| | | |
|---|---|---|
| GB | 2204398 | 11/1988 |
| JP | 2308800 | 12/1990 |
| JP | 3267000 | 11/1991 |
| JP | P4135497 | 5/1992 |
| JP | P4286957 | 10/1992 |
| WO | WO 88/04431 | 6/1988 |
| WO | WO 90/02334 | 3/1990 |
| WO | WO 94/03809 | 2/1994 |
| WO | WO 96/24062 | 8/1996 |
| WO | WO 98/36736 | 8/1998 |
| WO | WO 99/60399 | 11/1999 |
| WO | WO 00/72019 | 11/2000 |

OTHER PUBLICATIONS

Zuk et al., "Enzyme Immunochromatography–A Quantitative Immunoassay Requiring no Instrumentation," *Clin. Chem.*, 31(7):1144–50 (1985).

Heath–Fracica et al., Evaluation of New Latex Agglutination Test for Detection of Streptococcal Antibodies,*Diagn. Microbiol. Infect. Dis.*, 8:25–30 (1987).

Murray et al., "Chemically Modified Electrodes Molecular Design for Electranalysis," *Analytical Chemistry*, 59:379A–390A (1987).

Kannuck et al., "Measurement of Liposome–Released Ferrocyanide by a Dual–Function Polymer Modified Electrode," *Anal. Chemistry*, 60:142–147 (1988).

Durst et al., "Chemically Modified Electrode for Liposome–Mediated Homogeneous Immunoassay," 5th Symposium on Ion–Selective Electrodes, *Pergamon Press*, Oxford (1989).

Monroe, "Novel Liposome Immunoassays for Detecting Antigens, Antibodies and Haptens," *J. Liposome Res.*, 1:339–337 (1989–90).

Plant et al., "Generic Liposome Reagent for Immunoassays," *Anal. Biochem.*, 176:420–426 (1989).

Allen et al., "A Noninstrumented Quantitive Test System and Its Application for Determining Cholesterol Concentration in Whole Blood," *Clin. Chem.*, 36:1591–1597 (1990).

Durst et al., "Automated Liposome–Based Flow Injection Immunoassay System," GBF (Gesellschaft für Biotechnologische Forschung) Monographs, 14:181–190 (1990).

Locascio–Brown et al., "Liposome Flow Injection Immunoassay: Implications for Sensitivity, Dynamic Range, and Antibody Regeneration," *Analytical Chemistry*, pp. 2587–2593 (Dec. 1, 1990).

Collard–Bovy et al., "Microparticle–Enhanced Nephelometric Immunoassay. 1. Measurement of $\alpha s$–Casein and $\alpha$–Casein," *J. Dairy Sci.*, 74:3695–3701 (1991).

Yap et al., "Liposome Flow Injection Immunoassay: Model Calculations of Competitive Immunoreactions Involving Univalent and Multivalent Ligands," *Analytical Chemistry*, 63:2007–11 (1991).

Armbruster et al., "Screening for Drugs of Abuse with the Roche Ontrak Assays," *J. Anal. Tox.*, 16:172–175 (1992).

Durst et al., "Development of Liposome–Enhanced Immuno–Biosensing Devices for Field Measurements of Toxic Substances," *2ndBioelectroanalytical Symposium, Mátrafüred*, 1992, Akadémiai Kiadó, Budapest.

Pinnaduwage et al., "Stable Target–Sensitive Immunoliposomes," *Biochemistry*, 31:2850–2855 (1992).

Babbitt et al., "Contact–Dependent, Immunecomplex–Mediated Lysis of Hapten–Sensitized Liposomes," *Bioconjugate Chem.*, 4:199–205 (1993).

Durst et al., "Immunosensor for Extra–Lab Measurements Based on Liposome Amplification and Capillary Migration," *Biosensors & Bioelectronics*, 8:xiii–xv (1993).

Losso et al., "Development of a Particle Concentration Fluorescence Immunoassay for the Quantitative Determination of IgG in Bovine Milk," *J. Agric. Food Chem.*, 41:682–686 (1993).

Lou et al., "One–Step Competitive Immunochromatographic Assay for Semiquantitative Determination of Lipoprotein(a) in Plasma," *Clin. Chem.*, 39:619–624 (1993).

Parsons et al., "Multianalyte Assay System Developed for Drugs of Abuse," *Clin. Chem.*, 39:1899–1903 (1993).

Rosenzweig et al., "Laser–Based Particle–Counting Microimmunoassay for the Analysis of Single Human Erythrocytes," *Anal. Chem.*, 66:1771–1776 (1994).

Reeves et al., "Novel Optical Measurement Approach for the Quantitation of Liposome Immunomigration Assays," *Analytical Letters*, 28:2347–2352 (1995).

Roberts et al., "Investigation of Liposome–Based Immunomigration Sensors for the Detection of Polychlorinated Biphenyls," *Analytical Chemistry*, 67:482–491 (1995).

Siebert et al., "Liposome Immunomigration Field Assay Device for Alachlor Determination," *Analytica Chimica Acta*, 282:297–305 (1993).

Niwa et al., "Electrochemical Behavior of Reversible Redox Species at Interdigitated Array Electrodes with Different Geometries: Consideration of Redox Cycling and Collection Efficiency," *Anal. Chem.*, 62:447–452 (1990).

Niwa et al., "Small–Volume Voltammetric Detection of 4–Aminophenol with Interdigitated Array Electrodes and Its Application to Electronchemical Enzyme Immunoassay," *Anal. Chem.*, 65:1559–1563 (1993).

Rule et al., "Rapid Method for Visual Identification or Specific DNA Sequences Based on DNA–Tagged Liposomes,"*Clin. Chem.*, 42(8):1206–1209 (1996).

Rule et al., "Characteristics of DNA–Tagged Liposomes Allowing Their Use in Capillary–Migration, Sandwich–Hybridization Assays," *Anal. Biochem.*, 244:260–269 (1997).

Martorell et al., "Liposome Dehydration on Nitrocellulose and its Application in a Biotin Immunoassay," *Analytical Biochemistry* 271(2):177–185 (1999).

Madden et al., "Protection of Large Unilamellar Vesicles by Trehalose During Dehydration: Retention of Vesicle Contents," *Biochim. et Biophys. Acta*, 817:67–74 (1985).

Crowe et al., "Preservation of Freeze–Dried Liposomes by Trehalose," *Archives of Biochem. and Biophys.*, 242:240–247 (1985).

Harrigan et al., "Protection of Liposomes During Dehydration or Freezing," *Chemistry and Physics of Lipids*, 52:139–149 (1990).

Crowe et al., "Preservation of Liposomes by Freeze–Drying," in *Liposome Technology*, Gregoriadis, ed., CRC Press, Boca Raton, pp. 229–252 (1993).

Ausborn et al., "The Protective Effect of Free and Membrane–Bound Cryoprotectants During Freezing and Freeze–Drying of Liposomes," *J. of Controlled Release*, 30:105–116 (1994).

Durst, "Development of a Liposome–Enhanced Assay Format for the Detection of Specific Nucleic Acid Sequences," Cornell Center for Advanced Technology (CAT)—Biotechnology Program, Research Directory (1994–1995) (abstract).

Umeda et al., "Liposome Immune Lysis Assay (LILA). Application of Sandwich Method to Determine a Serum Protein Component With Antibody–Bearing Liposomes," *J. Immunol. Methods*, 95:15–21 (1986).

Umeda et al., "A Novel Liposome Immune Lysis Assay (LILA) for Determination of CRP Antigen Using Two Monoclonal Antibodies Recognizing Different Antigenic Determinants," *Acta Med. Okayama*, 48(6):299–304 (1994).

Ho et al., "Interactions of Target–Sensitive Immunoliposomes with Herpes Simplex Virus," *J. Biol. Chem.*, 262(29):13979–13984 (1987).

Singh et al., "Application of Antibody and Fluorophore–Derivatized Liposomes to Heterogeneous Immunoassays for D–dimer," *Biotechnol. Prog.*, 12:272–280 (1996).

Kung et al., "Large Liposome Agglutinaton Technique for the Serological Detection of Syphilis," *J. Immunol. Methods*, 90:189–196 (1986).

* cited by examiner

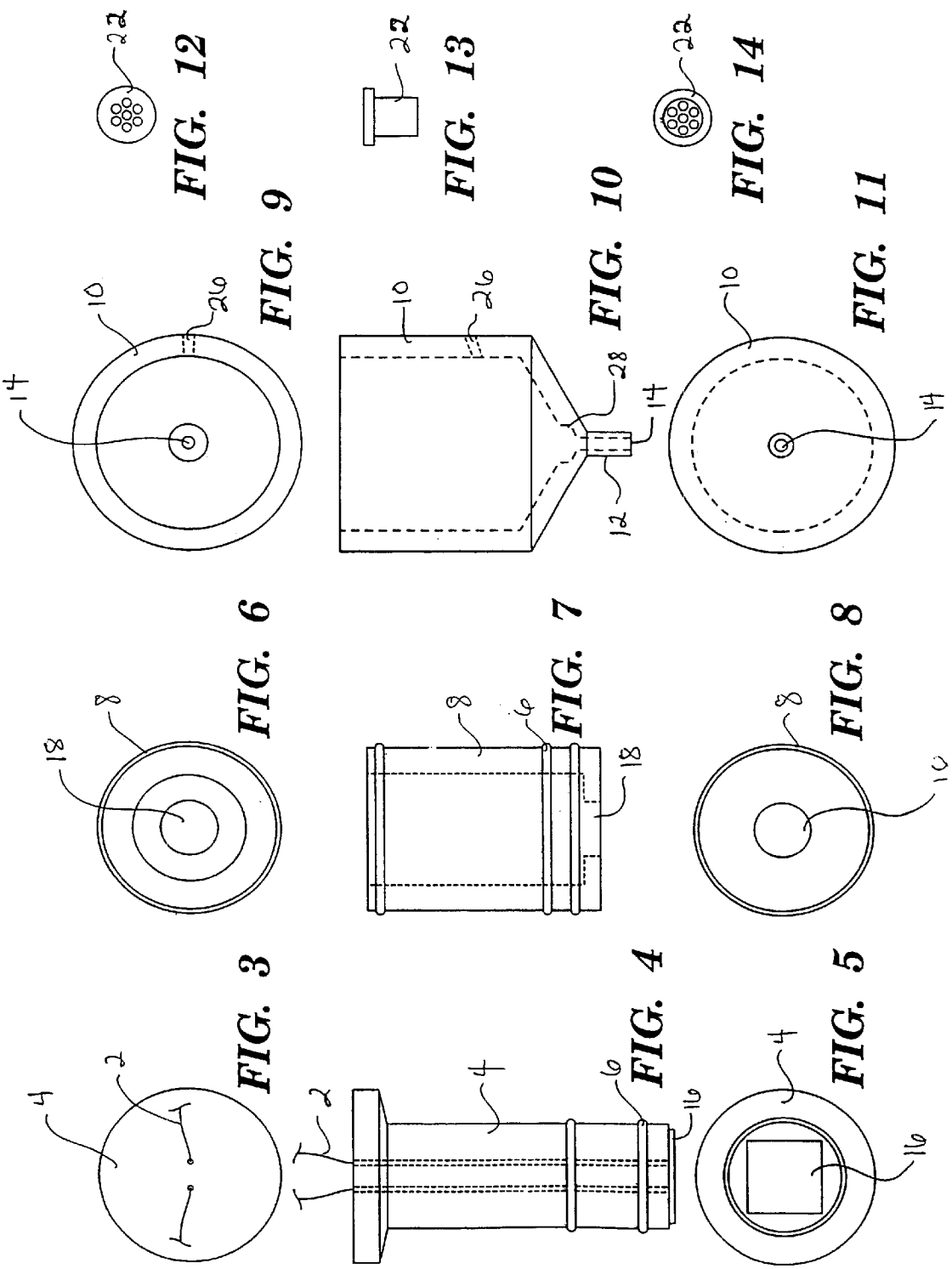

FILTRATION-DETECTION DEVICE AND METHOD OF USE

This application claims the benefit of U.S. Provisional Patent Application Ser. No. 60/162,371, filed Oct. 28, 1999, which is hereby incorporated by reference.

FIELD OF THE INVENTION

The present invention relates to a filtration-detection device, which can be used for rapid hybridization assays. Methods of using the device employ marker-loaded particles, e.g., liposomes, and either electrochemical or optical detection of an analyte in a test sample.

BACKGROUND OF THE INVENTION

Hybridization assays, in the form of enzyme-linked/radiolabel-linked nucleic acid probing (i.e. Southern and Northern blot analysis), have been widely used in the area of clinical diagnostic and research laboratory analysis for the detection of specific nucleic acid sequences. These methods offer high specificity, sensitivity, and ease of operation over other standard laboratory procedures. However, some of the disadvantages of the current probing technology which necessitate further improvement on the methodology include the lengthy time required for target-probe interaction, reagent additions, enzymatic conversion of substrate, and numerous washing steps between the various operations.

As an alternative to the use of enzymes or radioactivity, liposomes are of interest as detectable labels in hybridization assays because of their potential for immediate signal amplification. Liposomes are spherical vesicles in which an aqueous volume is enclosed by a bilayer membrane composed of phospholipid molecules (New, *Liposomes: A Practical Approach*, IRL Press, Oxford (1990)). Previous studies (Plant et al., *Anal. Biochem.*, 176:420–426 (1989); Durst et al., In: GBF Monograph Series, Schmid, Ed., VCH, Weinheim, FRG, vol. 14, pp. 181–190 (1990)) have demonstrated the advantages of liposome-encapsulated dye over enzymatically produced color in the enhancement of signals in competitive immunoassays. The capillary migration or lateral flow assays utilized in these experiments, avoid separation and washing steps and long incubation times and attains sensitivity and specificity comparable to enzyme-linked detection assays. Nevertheless, the methodologies (Siebert et al., *Anal. Chim. Acta*, 282:297–305 (1993); Roberts et al., *Anal. Chem.*, 67:482–491 (1995); Siebert et al., *Anal. Chim. Acta*, 311:309–318 (1995); Reeves et al., *Trends Anal. Chem.*, 14:351–355 (1995); Rule et al., *Clin. Chem.*, 42:1206–1209 (1996)) involve operations and solutions that make the handling of the sample and reagents susceptible to errors and more difficult to use for untrained personnel. Despite improvements in handling (U.S. Pat. No. 5,985,791 to Roberts et al.), lateral flow technologies have some limitations with regard to electrochemical detection.

The present invention is directed to overcoming the above-noted deficiencies in the prior art.

SUMMARY OF THE INVENTION

The present invention relates to a filtration-detection device for detecting or quantifying an analyte in a test sample. The filtration-detection device includes a filtration device having a first binding material immobilized thereto, wherein the first binding material is capable of binding to a portion of the analyte, and a detection assembly positioned relative to the filtration device to detect or quantify analyte bound to the first binding material.

The present invention also relates to a method for detecting or quantifying an analyte in a test sample. This method involves providing a filtration device having a first binding material immobilized thereto, wherein the first binding material is capable of binding to a portion of the analyte, providing a test mixture including the test sample and a binding material conjugate, wherein the binding material conjugate includes a second binding material bound to a first marker complex, the first marker complex includes a particle and a marker, and the second binding material is selected to bind with a portion of the analyte other than the portion of the analyte for which the first binding material is selected, passing the test mixture through the filtration device under conditions effective to permit reaction between any analyte present and the first and second binding materials, detecting the presence or amount of the marker on the filtration device using a detection assembly, and correlating the presence or amount of the marker on the filtration device with the presence or amount, respectively, of the analyte in the test sample.

The present invention further provides a method for detecting or quantifying an analyte in a test sample involving providing a filtration device having a first binding material immobilized thereto, wherein the first binding material is capable of binding to a portion of the analyte, providing a test mixture including the test sample and an analyte analog conjugate, wherein the analyte analog conjugate includes an analyte analog bound to a first marker complex, and the first marker complex includes a particle and a marker, passing the test mixture through the filtration device under conditions effective to permit competition to occur between any analyte present and the analyte analog conjugate for the first binding material, detecting the presence or amount of the marker on the filtration device using a detection assembly, and correlating the presence or amount of the marker on the filtration device with the presence or amount, respectively, of the analyte in the test sample.

The present invention also relates to a method for detecting or quantifying the amount of an analyte in a test sample which includes providing a test mixture including the test sample, a first conjugate including a first binding material bound to a first marker complex, wherein the first marker complex includes a particle and a marker, and wherein the first binding material is selected to bind with a portion of the analyte, and a second conjugate including a second binding material bound to a second marker complex, wherein the second marker complex includes a particle and a marker, and wherein the second binding material is selected to bind with a portion of the analyte other than the portion of the analyte for which the first binding material is selected, permitting reaction to occur in the test mixture between any analyte present and the first and second binding materials to form a first conjugate-analyte-second conjugate aggregate, collecting the aggregate on a filtration device, detecting the presence or amount of the marker on the filtration device using a detection device, and correlating the presence or amount of the marker on the filtration device with the presence or amount, respectively, of the analyte in the test sample.

The device and methods of the invention can be used directly in the field. The device can be used repeatedly or can be used only once. When used only once, the device can be free from residual environmental contaminants other than what may be present in the sample to be measured. Samples can be assayed within minutes after collection, with the results immediately available on-site. In addition, the device and methods of the invention are less complex than many of the prior materials and methods. The ability to deliver quantitative results without additional steps for spectrophotometric or fluorometric analysis is an advantage of the present electrochemical device and method over devices and methods that employ dyes and fluorescent materials as markers.

In addition, in one embodiment of the invention, electroactive marker-loaded liposomes as used in the device and method of the invention provide a highly sensitive, rapid, or even instantaneous signal production/amplification system. Furthermore, in some embodiments of the invention, the amount of marker measured on the filtration device of the test device is directly proportional to the analyte concentration in the sample. This feature of the invention provides a particular advantage over prior test devices, nucleic acid detection assays, and immunoassays, providing an intuitive correlation between signal strength and analyte concentration. Electrochemical detection offers greater sensitivity than colorimetric determination and is comparable to fluorometry or chemiluminescence. In addition, the present invention provides quantitative results that can be obtained directly from the electroanalyzer or other detection instrumentation to which the test device is connected, without the need to transfer the device to a separate optical measurement device. Also, electrochemical detection allows for testing in solutions or mixtures that are highly colored or include particulate matter, for which optical detection may be unsuitable.

Interdigitated electrode arrays are particularly suitable for the test device and methods of the present invention due to their planar configuration and their inherent sensitivity for electrochemical measurements. Microelectrodes fabricated in an interdigitated array have inherent advantages in signal detection over more conventional electrode configurations. These advantages can only be realized with electrodes of very small dimensions due to the theoretical relationships between electrode geometry and ionic diffusion. Scaling down the size of an individual electrode has the advantage of increasing the rate of mass transport, increasing the signal-to-noise (faradaic/charging current) ratio, and decreasing ohmic signal losses, as described in Fleischmann et al., Eds. *Ultramicroelectrodes*, Datatech Systems, Inc., Morganton, N.C. (1987), which is hereby incorporated by reference. Advantages of microelectrodes are also described in Howell, *Voltammetric Microelectrodes*, Bioanalytical Systems, Inc., West Lafayette, Ind. 47906, which is hereby incorporated by reference.

Advantages of fabricating small electrodes in interdigitated arrays go even further by allowing redox cycling of ions back and forth between anode(s) and cathode(s). See Niwa et al., *Anal. Chem.* 65:1559–1563 (1993) and Niwa et al., *Anal. Chem.* 66:285–289 (1994), each of which is hereby incorporated by reference. This generates much larger currents for detection and allows for the use of extremely small sample volumes. By using a dual potentiostat and a four-electrode system with an interdigitated array, it is possible to almost completely eliminate charging current. This results in a greater signal-to-noise ratio and allows for the use of extremely high scan rates. See Niwa et al., *Anal. Chem.* 62:447–452 (1990) and Chidsay et al., *Anal. Chem.* 58:601–607 (1986), which are hereby incorporated by reference. Furthermore, the sophisticated electronics needed to detect the very small currents associated with individual microelectrode filaments are not necessary due to the summation of current from the large array of microelectrodes.

BRIEF DESCRIPTION OF THE DRAWINGS

FIG. 3 shows a top view of an inner stem (4).

FIG. 4 shows a side view of an inner stem (4).

FIG. 5 shows a bottom view of an inner stem (4).

FIG. 6 shows a top view of an inner housing (8).

FIG. 7 shows a side view of an inner housing (8).

FIG. 8 shows a bottom view of an inner housing (8).

FIG. 9 shows a top view of an outer housing (10).

FIG. 10 shows a side view of an outer housing (10).

FIG. 11 shows a bottom view of an outer housing (10).

FIG. 12 shows a top view of a membrane holder (22).

FIG. 13 shows a side view of a membrane holder (22).

FIG. 14 shows a bottom view of a membrane holder (22).

DETAILED DESCRIPTION OF THE INVENTION

Figure 1:
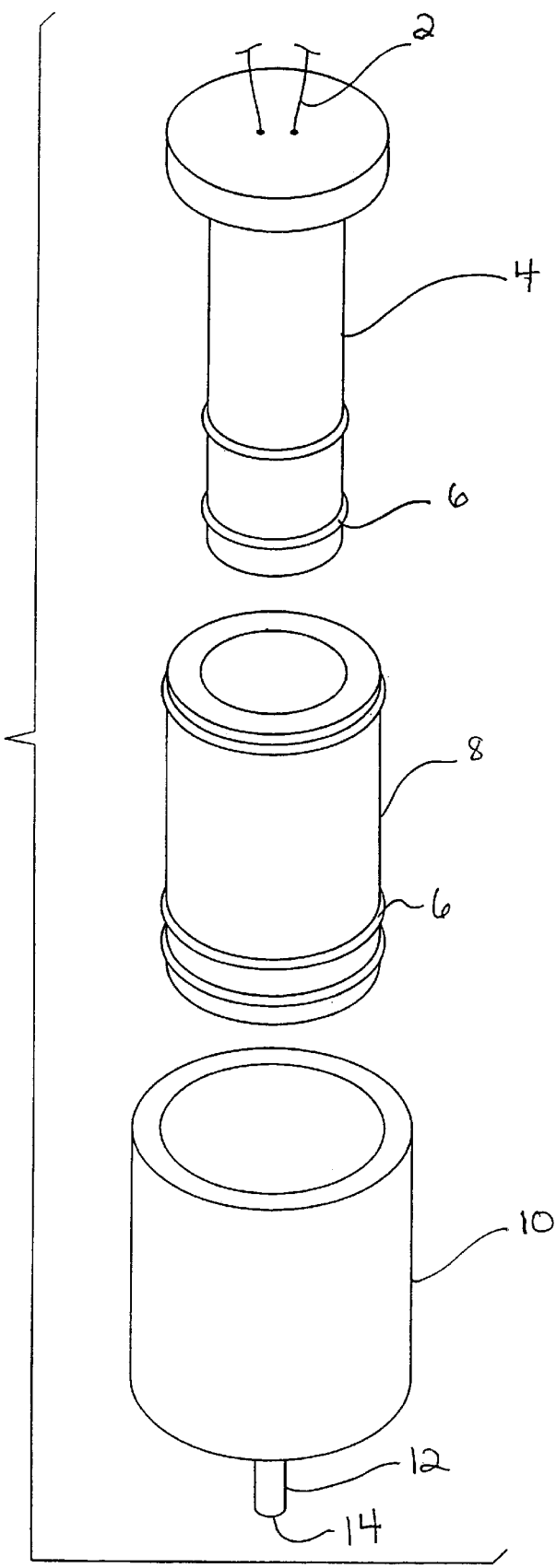
FIG. 1 shows an exploded perspective view of the filtration-detection device of the present invention.

As described above, the present invention relates to a filtration-detection device for detecting or quantifying an analyte in a test sample. The filtration-detection device includes a filtration device having a first binding material immobilized thereto, wherein the first binding material is capable of binding to a portion of the analyte, and a detection assembly positioned relative to the filtration device to detect or quantify analyte bound to the first binding material.

The present invention also relates to a method for detecting or quantifying an analyte in a test sample. This method involves providing a filtration device having a first binding material immobilized thereto, wherein the first binding material is capable of binding to a portion of the analyte, providing a test mixture including the test sample and a binding material conjugate, wherein the binding material conjugate includes a second binding material bound to a first marker complex, the first marker complex includes a particle and a marker, and the second binding material is selected to bind with a portion of the analyte other than the portion of the analyte for which the first binding material is selected, passing the test mixture through the filtration device under conditions effective to permit reaction between any analyte present and the first and second binding materials, detecting the presence or amount of the marker on the filtration device using a detection assembly, and correlating the presence or amount of the marker on the filtration device with the presence or amount, respectively, of the analyte in the test sample.

The present invention further provides a method for detecting or quantifying an analyte in a test sample involving providing a filtration device having a first binding material immobilized thereto, wherein the first binding material is capable of binding to a portion of the analyte, providing a test mixture including the test sample and an analyte analog conjugate, wherein the analyte analog conjugate includes an analyte analog bound to a first marker complex, and the first marker complex includes a particle and a marker, passing the test mixture through the filtration device under conditions effective to permit competition to occur between any analyte present and the analyte analog conjugate for the first binding material, detecting the presence or amount of the marker on the filtration device using a detection assembly, and correlating the presence or amount of the marker on the filtration device with the presence or amount, respectively, of the analyte in the test sample.

The present invention also relates to a method for detecting or quantifying the amount of an analyte in a test sample which includes providing a test mixture including the test sample, a first conjugate including a first binding material bound to a first marker complex, wherein the first marker complex includes a particle and a marker, and wherein the first binding material is selected to bind with a portion of the analyte, and a second conjugate including a second binding material bound to a second marker complex, wherein the second marker complex includes a particle and a marker, and wherein the second binding material is selected to bind with a portion of the analyte other than the portion of the analyte for which the first binding material is selected, permitting reaction to occur in the test mixture between any analyte present and the first and second binding materials to form a first conjugate-analyte-second conjugate aggregate, collecting the aggregate on a filtration device, detecting the presence or amount of the marker on the filtration device using a detection device, and correlating the presence or amount of the marker on the filtration device with the presence or amount, respectively, of the analyte in the test sample.

By "analyte" is meant the compound or composition to be measured or detected. Suitable analytes include, but are not limited to, antigens (e.g., protein antigens), haptens, and target nucleic acid molecules. A preferred analyte is a target nucleic acid molecule. A more preferred analyte is a target nucleic acid molecule found in an organism selected from the group consisting of bacteria, fungi, viruses, protozoa, parasites, animals (e.g., humans), and plants. Suitable organisms include, but are not limited to, *Cryptosporidium parvum, Escherichia coli*, Dengue virus, and Human immunodeficiency virus (HIV-1). In a most preferred embodiment of the invention, the analyte is a target nucleic acid molecule from *Cryplosporidium parvum*.

In one embodiment, the test device and methods of the present invention include immobilizing a first binding material specific for the analyte on the filtration device. The first binding material is capable of binding to a portion of the analyte as the test mixture is passed through the filtration device.

By "binding material" is meant a bioreceptor molecule such as an immunoglobulin or derivative or fragment thereof having an area on the surface or in a cavity which specifically binds to and is thereby defined as complementary with a particular spatial and polar organization of another molecule—in this case, the analyte. Suitable binding materials include antibodies, antigens, nucleic acid molecules, aptamers, cell receptors, biotin, streptavidin, and other suitable ligands. When the analyte is a target nucleic acid molecule, the first binding material can be a nucleic acid molecule (i.e., capture probe, selected to hybridize with a portion of the target nucleic acid molecule) or other moiety, such as an antibody or other agent capable of binding to and interacting with the analyte.

Antibody binding materials can be monoclonal or polyclonal or genetically engineered (e.g., single-chain antibodies, catalytic antibodies) and can be prepared by techniques that are well known in the art such as immunization of a host and collection of sera or hybrid cell line technology or by genetic engineering. The binding material may also be any naturally occurring or synthetic compound that specifically binds the analyte of interest.

In one embodiment of the present invention, an analyte analog conjugate is used. This embodiment is particularly suitable for use of the test device in a competitive binding assay. Certain analytes of interest may be so intractable as to make direct conjugation with the particle inconvenient, difficult, or even impossible. In such cases, it will be necessary to employ a reactive analog of the analyte of interest to prepare the analyte analog conjugate. Thus, by "analyte analog" is meant the analyte or an analog of which will react with or bind to the particle. When an analog is employed, however, it is necessary that the particular characteristics of the analyte necessary for recognition by the first binding material in the competition reaction be present in the analyte analog conjugated with the marker complex.

As discussed in greater detail below, the methods of the present invention may employ a second binding material bound to a marker complex which includes a particle and a marker.

When present, the first and second binding materials are selected to bind specifically to separate portions of the analyte. For example, when the analyte is a nucleic acid sequence, it is necessary to choose probes for separate portions of the target nucleic acid sequence. Techniques for designing such probes are well-known. Probes suitable for the practice of the present invention must be complementary to a portion of the target analyte sequence, i.e., capable of hybridizing to the target, and should be highly specific for the target analyte. The probes are preferably between 17 and 25 nucleotides long but can be longer or shorter, to provide the requisite specificity while avoiding unduly long hybridization times and minimizing the potential for formation of secondary structures under the assay conditions. In addition, in this example, the first and second binding materials (capture and reporter probes, respectively) should not be capable of hybridizing with one another or in any other way interacting with one another. Techniques for identifying probes and reaction conditions suitable for the practice of the invention are described in Sambrook et al., *Molecular Cloning: A Laboratory Manual*, Cold Spring Harbor Laboratory Press (1989), which is hereby incorporated by reference. A software program known as "Lasergene", available from DNASTAR, may optionally be used.

In general, to design an assay when the analyte is a target nucleic acid molecule, the target nucleic acid is extracted from a sample, and then amplified by one of a variety of known amplification techniques. Such amplification techniques include polymerase chain reaction, ligase chain reaction, and Nucleic Acid Sequence Based Amplification (NASBA). See Kievits et al., "NASBA Isothermal Enzymatic in vitro Nucleic Acid Amplification Optimized for the Diagnosis of HIV-1 Infection" *J. of Virological Methods* 35:273–286 (1991), which is hereby incorporated by reference. NASBA, marketed by Organon-Teknika, is a preferred amplification technique when determining information regarding the presence or concentration of viable organisms in a sample.

As described above, the first binding material, second binding material, and/or analyte analog may be bound to a marker complex which includes a particle and a marker. Suitable particles include liposomes (the marker may be encapsulated within the liposome, in the bilayer, or attached to the liposome membrane surface), latex beads, gold particles, silica particles, dendrimers, magnetic beads (e.g., antibody-tagged magnetic beads and nucleic acid probe-tagged magnetic beads), or any other particle suitable for derivatization.

In a preferred embodiment, the particle is a liposome encapsulating a marker. The first binding material, second binding material, and/or analyte analog may be conjugated to the liposome surface. The first binding material and/or second binding material must be bound to the liposome or other particle so as to present a portion of the first binding material and/or second binding material that may be recognized by the analyte.

Suitable conjugation methods are discussed in U.S. Pat. Nos. 5,789,154, 5,756,362, and 5,753,519, which are hereby incorporated by reference. For example, the liposome surface may be activated with thiol groups and coupled to a maleimide group on the second binding material. Conversely, maleimide-activated liposomes and thiol group-activated second binding material may be employed. In addition, it is possible to couple a nucleic acid sequence to the liposome surface using either of the above methods such that the bound sequence is complementary to and capable of hybridizing to a portion of the second binding material (reporter probe), allowing the remaining portion of the second binding material to interact with and hybridize with a portion of the target sequence.

As hereinabove indicated, the present invention employs a marker complex which includes a particle and a marker, e.g., a marker within the interior of the liposomes. Suitable markers include fluorescent dyes, visible dyes, bio- and chemiluminescent materials, enzymes, enzymatic substrates, and electroactive markers. Visible dyes can be measured without lysis of the liposomes. Lysis of the liposomes in the filtration-detection device of the present invention may be accomplished by applying a liposome lysing agent to the filtration device. Suitable liposome lysing materials include surfactants such as octylglucopyranoside, sodium dioxycholate, sodium dodecylsulfate, polyoxyethylenesorbitan monolaurate sold by Sigma under the trademark TWEEN-20, and a non-ionic surfactant sold by Sigma under the trademark TRITON X-100, which is t-octylphenoxypolyethoxyethanol. Octylglucopyranoside is a preferred lysing agent for many assays, because it lyses liposomes rapidly and does not appear to interfere with signal measurement. Alternatively, complement lysis of liposomes may be employed, or the liposomes can be ruptured with electrical, optical, thermal, or other physical means.

Preferably, the marker in the first marker complex and second marker complex is the same.

A qualitative or semi-quantitative measurement of the presence or amount of an analyte of interest may be made with the unaided eye when visible dyes are used as the marker. Alternatively, when greater precision is desired, or when the marker used necessitates instrumental analysis, the intensity of the marker may be measured directly on the filter membrane using a quantitative instrument such as a reflectometer, fluorometer, spectrophotometer, etc.

In one embodiment of the invention, a marker which is visible under the assay conditions is used so that the presence and/or amount of analyte may be determined without further treatment and without the use of instrumentation, e.g., by use of liposomes containing a dye as the marker.

Alternatively, the methods and test device of the present invention may be modified to use an electrochemical marker. Suitable electrochemical markers, as well as methods for selecting them and using them are disclosed in U.S. Pat. No. 5,958,791 to Roberts et al. and co-pending U.S. patent application Ser. No. 09/315,576, filed May 20, 1999, which are hereby incorporated by reference. In one embodiment, the electrochemical marker is a reversible redox couple. A reversible redox couple consists of chemical species for which the heterogenous electron transfer rate is rapid and the redox reaction exhibits minimal overpotential. Suitable examples of a reversible redox couple include, but are not limited to, ferrocene derivatives, ferrocinium derivatives, mixtures of ferrocene derivatives and ferrocinium derivatives, cupric chloride, cuprous chloride, mixtures of cupric chloride and cuprous chloride, ruthenium-tris-bipyridine, potassium ferrohexacyanide, potassium ferrihexacyanide, and mixtures of potassium ferrohexacyanide and potassium ferrihexacyanide. Preferably, the electrochemical marker is encapsulated within a liposome, in the bilayer, or attached to a liposome membrane surface.

Referring to FIG. 1, the filtration-detection device of the present invention includes a detection assembly, including an inner stem (4) and inner housing (8), and a filtration device, including an outer housing (10). A wide variety of organic and inorganic materials, both natural and synthetic, and combinations thereof, may be employed for the components of the filtration-detection device, provided only that the filtration-detection device does not interfere with the production of signal from the marker. Illustrative polymers include polyethylene, polypropylene, poly(4-methylbutene), polystyrene, polymethacrylate, poly(ethylene terephthalate), nylon, poly(vinyl chloride) poly(vinyl butyrate), glass, ceramics, metals, and the like.

The filtration device of the present invention includes an outer housing (10), which includes an inlet hole (26) for a pipette (24), an outlet (12) with an outlet hole (14), and a support for a membrane holder (28) (see FIGS. 1, 2, 9–11, 15, and 16). The filtration device also includes a membrane holder (22) (see FIGS. 12–14) which supports a membrane (20) (see FIG. 2). The membrane holder (22) will normally be hydrophobic, water insoluble, non-porous, and rigid, one surface of which usually will be the same dimensions as the membrane (20). The membrane (20) rests on top of the membrane holder (22) which in turn rests on top of the membrane holder support (28) region of the outer housing (10). The outer housing (10) has an inlet hole (26) that allows insertion of a pipette tip (24) for the application of test mixture, liposome lysing agents, buffers, and the like into the filtration device. Material that is not retained on the membrane (20) passes through an outlet (12) and is collected from the liquid outlet (14).

The membrane supported by the membrane holder (22) is a filter membrane, i.e., a porous material having a pore size of from about 0.1 $\mu$m to about 100 $\mu$m, preferably from about 2 $\mu$m to about 30 $\mu$m, which allows an aqueous medium to flow therethrough. The pore size has an important impact on the performance of the device. The pore size has to be larger than the mean diameter of marker complexes (i.e., signal producing elements used). Also, the pores should not be too large so that a good volume to surface ratio can be obtained. Additionally, the membrane material must allow the retaining of the first conjugate-analyte-second conjugate aggregate (or other signal producing elements)

when desired and the flow through of signal producing elements when desired. Manufacturers of membranes include Schleicher & Schuell, Pall/Gelman, Sartorius, Whatman, and Millipore. Preferably, the membrane of the filtration device allows components of the test mixture not bound to the first binding material and/or second binding material to flow through.

Suitable filter membranes for the device and methods of the invention include nitrocellulose membranes, nitrocellulose mixed esters, mylar membranes, polysulfonyl based membranes, plain filter paper, glass fiber membranes, and membranes of any plastic material with defined pore size, such as polycarbonate filters, porous gold, and porous magnetic material. It is to be understood that the term "nitrocellulose" refers to nitric acid esters of cellulose, which may be nitrocellulose alone, or a mixed ester of nitric acid and other acids, and in particular, aliphatic carboxylic acids having from one to seven carbon atoms, with acetic acid being preferred. Such materials, which are formed from cellulose esterified with nitric acid alone, or a mixture of nitric acid and another acid such as acetic acid, are often referred to as nitrocellulose paper. The filter membranes can be of a variety of shapes, including rectangular, circular, oval, trigonal, or the like.

To permit for conservation of reagents and provide for samples of limited size, the dimensions of the filtration detection device and, in particular, of the filter membrane are preferably relatively small. Generally, the width of the filter membrane will be from about 1 mm to about 20 mm and the length of the filter membrane will be from about 1 mm to about 20 mm.

As described above, in one embodiment of the present invention, the filtration device, preferably the filter membrane, has a first binding material immobilized thereto. Thus, the filter membrane may be polyfunctional or be capable of being polyfunctionalized to permit immobilization of the first binding material.

Materials having a surface area sufficient for supporting the binding material and any other agents to be immobilized thereon as described herein may be employed for producing test devices in accordance with the present invention, and the material must allow the passage of liquid therethrough, i.e., the passage of liquid from one side of the membrane, through the membrane, to the other side of the membrane.

Filter membranes having high surface areas (such as nitrocellulose) are particularly preferred for some applications in that the first binding material may be supported on such materials in high concentrations. It is to be understood, however, that the concentration of binding material which is actually used is dependent in part on the binding affinity of the first binding material. Accordingly, the scope of the invention is not limited to a particular concentration of first binding material on the filter membrane.

Application of the first binding material to the filter membrane may be ccomplished by well-known techniques, for example, by spraying, printing, or spotting solutions of this component onto the filter membrane.

The first binding material can be bound to the filter membrane by covalent bonding. For example, the material to be bound can be applied directly to the filter membrane, and then bonded thereto via ultraviolet radiation. Alternatively, materials can be adsorbed onto the filter membrane, as long as the binding of the first binding material to the filter membrane is non-diffusive. This will involve contacting the filter membrane with a solution containing the material to be bound to the filter membrane and allowing the filter membrane to dry. In general, this procedure will be useful only where the filter membrane is relatively hydrophobic or has a high surface charge, and subsequent treatment with proteins, detergents, polysaccharides, or other materials capable of blocking nonspecific binding sites will be required.

In one embodiment, the first binding material is indirectly bound to the filter membrane. For example, the first binding material is preferably labeled with a tag, for example, biotin, and a ligand that specifically binds the tag, for example, streptavidin or anti-biotin antibody, is premixed with the first binding material labeled with the tag and then applied to the filter membrane. Other agents suitable for immobilizing the first binding material on the filter membrane include any compounds or antibodies that specifically bind a chosen tag used as a label for the first binding material, e.g., avidin, anti-fluorescein, anti-digoxin, and anti-dinitrophenyl (DNP).

Before or after application of the first binding material to the filter membrane, the residual nonspecific binding capacity of the filter membrane can be, and preferably is, saturated or blocked with blocking agents which typically include a combination of three compounds: proteins, synthetic polymers, and surfactants, and which do not specifically bind the materials to be employed in the assay. Blocking is generally carried out after the first binding material is applied to the filter membrane, but it may be possible to block the filter membrane before this component is applied depending on the method of application, the particular blocking agent, and filter membrane employed. Thus, for example, the residual binding capacity of the filter membrane may be blocked so as to prevent nonspecific binding by the use of bovine serum albumin, as described in Towbin et al., *Proc. Nat'l. Acad. Sci.*, 76:4350 (1979), which is hereby incorporated by reference. The techniques for preventing non-specific binding are generally known in the art, and such techniques are also generally applicable to preventing nonspecific binding in the assay of the present invention. Examples of particularly suitable techniques for blocking with polyvinylpyrrolidone and polyvinylalcohol are described in, for example, Bartles et al., *Anal. Biochem.*, 140:784 (1984), and in British Pat. Specification GB 2204398 A, respectively, which are hereby incorporated by reference. Alternatively, one or more blocking agents can be incorporated into the buffer solution used to wash or carry test components into the filtration device (i.e., onto the filter membrane).

The blocking agents block nonspecific binding sites on the filter membrane. Thus, preferred blocking agents preferentially bind to the filter membrane. The blocking agents are selected from the group consisting of proteinaceous blocking reagents capable of inhibiting binding of molecules having a molecular weight of greater than about 1000 with said filter membrane and polymer blocking reagents capable of inhibiting binding of molecules having a molecular weight of less than about 1000 with said filter membrane. The proteinaceous blocking reagent may be selected from the group consisting of, but no limited to, gelatin, non-fat dry milk, bovine serum albumin. albumins from other sources, keyhold limpet hemocyanin, casein, gum arabic, fish gelatin, ovalbumin, and horse serum. The polymer blocking reagent may be selected from the group consisting of polyvinylpyrrolidone, polyvinyl alcohol, and hydroxypropylmethyl cellulose. The blocking reagent is preferably a mixture of the above-identified blocking reagents.

Preferably, the blocking agents include a combination of polyvinylpyrrolidone and one or a mixture of proteins, such as gelatin, non-fat dry milk, bovine serum albumin, and casein. Preferred concentrations of blocking agents include from about 0.01 w/v % to about 1 w/v % polyvinylpyrrolidone, from about 0.01 w/v % to about 1 w/v % gelatin, from about 0.0001 w/v % to about 0.1 w/v % casein, from about 0.005 w/v % to about 1 w/v % non-fat dry milk, from about 0.001 w/v % to about 1 w/v% bovine serum albumin, and from about 0.001 w/v% to about 1 w/v % methylated bovine serum albumin.

In conjunction with a blocking reagent or reagents, a surfactant may be applied to the filter membrane. Suitable surfactants include BRIJ™ (polyoxyethylene ether), TWEEN 20™ (polyoxyethylenesorbitan monolaurate), TRITON X-100™ (t-octylphenoxypolyethoxyethanol), sodium dodecylsulfate, n-octyl-D-glucopyranoside, SPAN 20™, NONINDET P-40, CHAPSO™, TURGITOL™ and sodiurm dioxycholate. The concentration of the surfactant(s) employed in a blocking solution will depend, in part, upon the particle, e.g., liposome, composition. In general, surfactants may be incorporated in a concentration of from about 0 to about 0.01 volume percent of the blocking solution, preferably from about 0.001 to about 0.005 volume percent of the blocking solution. It is important that the concentration of surfactant applied to the filter material be controlled, as premature lysis of liposomes may occur if the surfactant concentration is too high. Preferred surfactants include polyoxyethylene ethers, polyoxyethylenesorbitan monolaurate, t-octylphenoxypolyethoxyethanol, sodium dodecylsulfate, octylglucopyranoside, and sodium dioxycholate.

Blocking agents are applied in a buffer solution to the filter membrane. Suitable buffers solutions include Tris (hydroxymethyl)aminomethane/HCl (Tris/HCl), Tris/citrate, Tris/maleate, Tris/glycine, phosphate buffer, HEPES, and other biological buffers in the correct pH range.

In some cases, a pre-wash of the membrane is recommended (e.g. in the case of Sartorius membranes). This pre-wash can be done, for example in a 0.02 M Tris-HCL buffer containing 150 mM NaCl, pH 7.0 containing 5% methanol.

Figure 2:
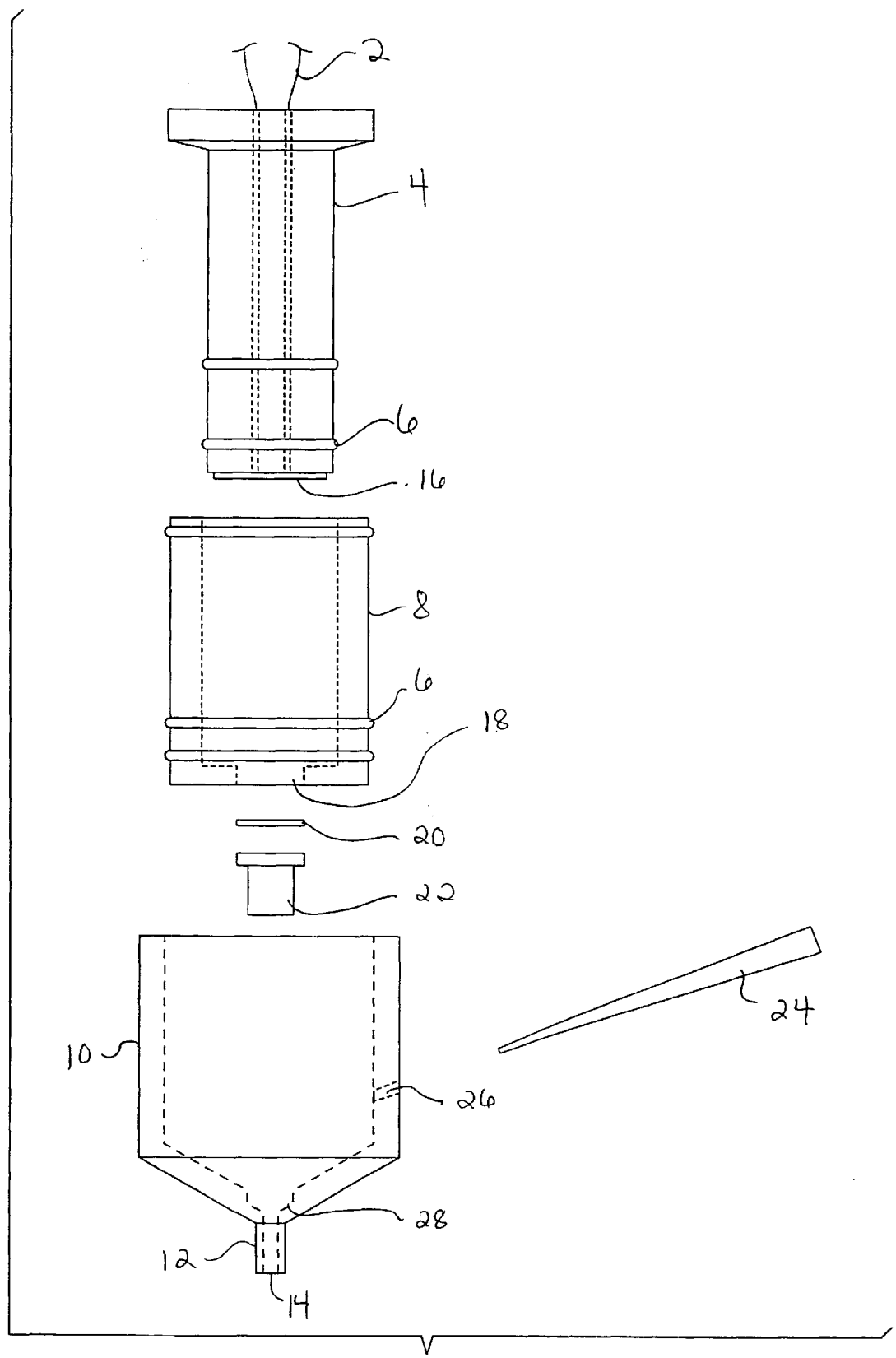
FIG. 2 shows an exploded side view of an inner stem (4), inner housing (8), and outer housing (10) of the filtration-detection device of the present invention.
Figure 15:
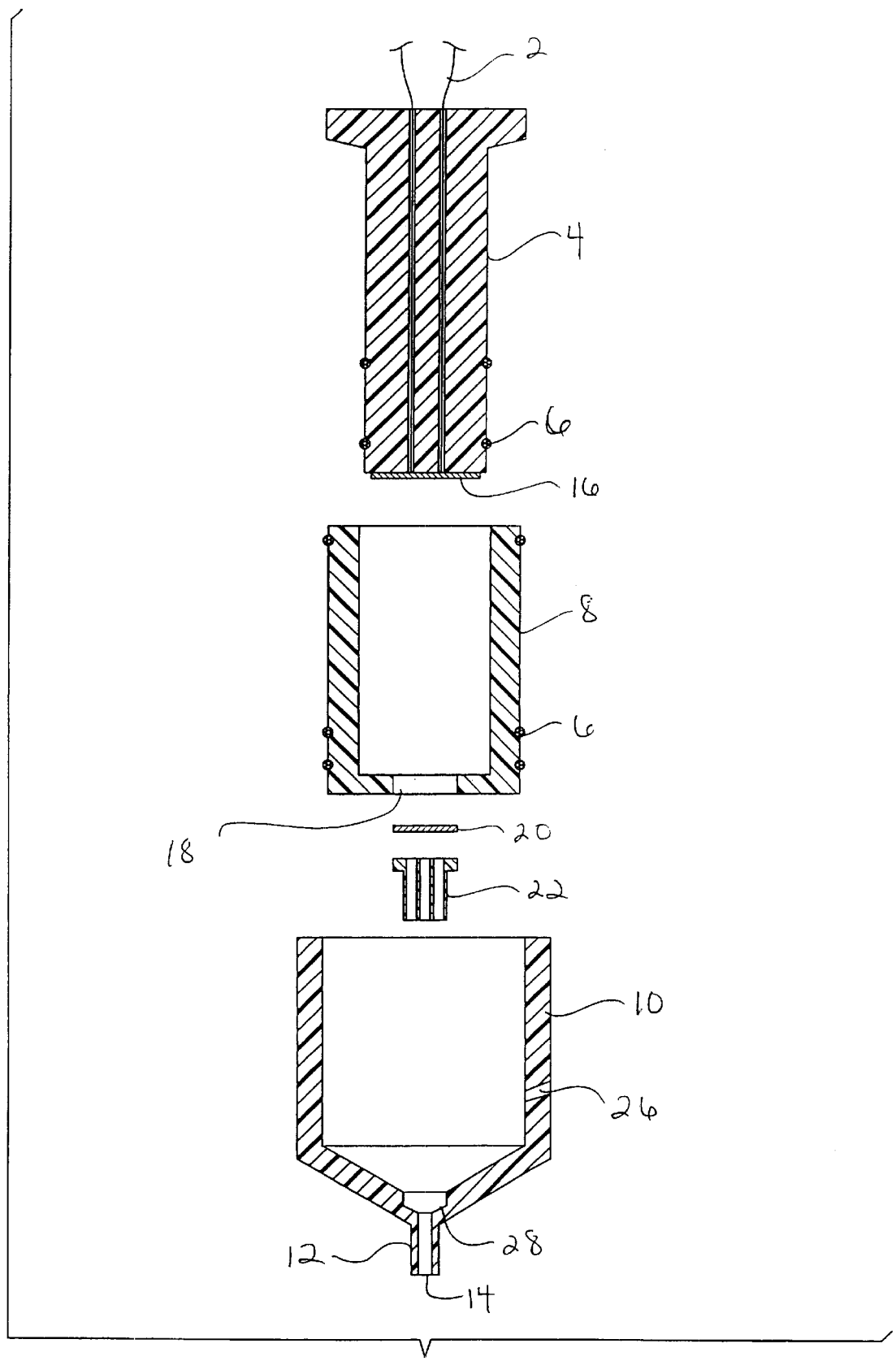
FIG. 15 shows an exploded cross-sectional side view of an inner stem (4), inner housing (8), and outer housing (10) of the filtration-detection device of the present invention.
Figure 16:
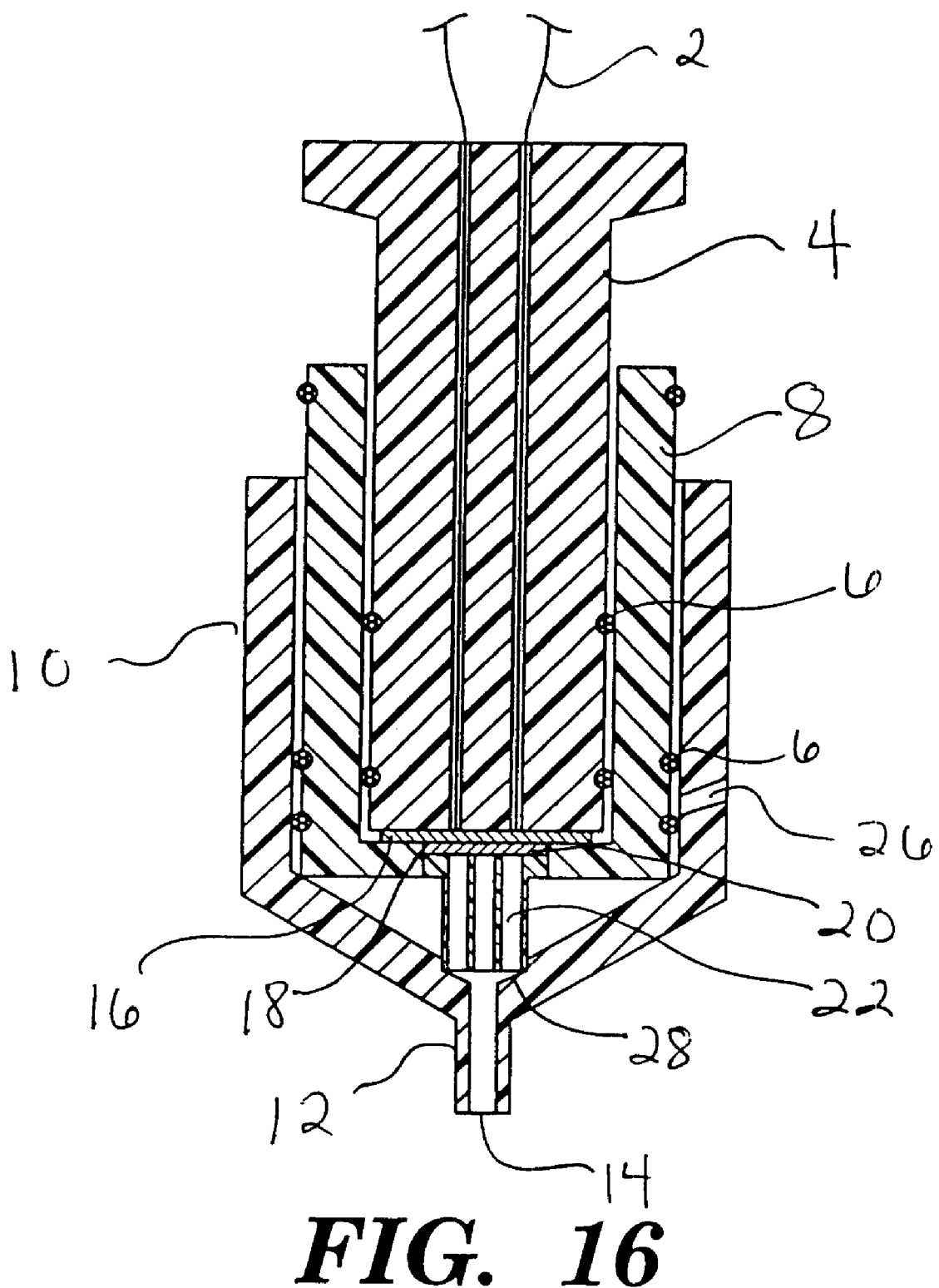
FIG. 16 shows a cross-sectional side view of an inner stem (4), inner housing (8), and outer housing (10) of the filtration-detection device of the present invention.

The filtration-detection device of the present invention includes a detection assembly. The detection assembly of the present invention includes an inner stem (4) and an inner housing (8) (FIGS. 1 and 2).

As described above, suitable detection assemblies include any device for detecting the presence of the marker, such as the unaided eye, instruments for optical detection, and instruments for electrochemical detection.

In a preferred embodiment of the invention, the detection assembly is in contact with the filtration device, at least during signal detection and/or measurement.

In one embodiment of the present invention, the detection assembly is an optical detection assembly.

In another embodiment, the detection assembly is an electrochemical detection assembly. As shown in FIGS. 3–5, the inner stem (4) of the electrochemical detection assembly includes contact wires (2), at least one o-ring or any other means to provide insulation (6), and an electrochemical detection device (16). The inner housing (8) includes at least one o-ring or other means to provide insulation (6) on its surface and an opening for a membrane (18) on its lower edge to insert a membrane (20) which is placed on a membrane holder (22) (FIGS. 6–8, 15–16).

In a preferred embodiment, the electrochemical detection device includes an electrode array including a first conductor and a second conductor. Each conductor (or electrode) comprises a plurality of fingers interdigitated with the fingers of the other conductor.

In one embodiment, the first and second conductors comprise from about 2 to about 2000 fingers. In another embodiment, the first and second conductors comprise one or more materials selected from the group consisting of platinum, gold, graphite, and silver. The first conductor may be composed of the same or a different material from the second conductor.

In another embodiment, the first and second conductors may further include a binder material to bind the first and second conductors to a support (described below). Suitable binder materials include, but are not limited to titanium, chromium, wolfram, and tungsten. The binder materials are completely covered with the conductor materials described above and, thus, do not contribute to the electrochemical reaction.

Preferably, the fingers of each of the conductors are from about 1 $\mu$m to about 20 $\mu$m wide and are spaced from about 1 nm to 10 $\mu$m apart, preferably, from about 0.5 $\mu$m to 10 $\mu$m apart, although other dimensions may be used.

In one embodiment, the first and second conductors include contact pads from which the fingers emerge and through which the fingers are electrically connected to the voltage source. Preferably, the contact pads of the first and second conductors are at least partially coated with an insulating material.

The first and second conductors are electrically connected to one another via a voltage source and readout device, and the electrode array is positioned to induce redox cycling of an electroactive marker.

In another embodiment, the electrochemical detection device includes a reference electrode in electrical contact with the electrode array. The reference electrode will usually be a silver electrode, although other alternatives, such as lead, may be used for the reference electrode. In a three electrode format, the potential of either the first or second conductor is controlled versus the reference electrode, and the potential of the other of the first or second conductors "floats" to maintain the same current through both of the electrodes. The magnitude of the current flowing between the first and second conductors is measured and correlated to the amount of the analyte, as the measured current is proportional to the marker ion concentration.

In another optional embodiment, a "four-electrode" system comprising the interdigitated array, a reference electrode, and an auxiliary electrode can be employed. A four-electrode system is described in Niwa et al., *Anal. Chem.* 62:447–452 (1990), which is hereby incorporated by reference. Platinum is a suitable material for the auxiliary electrode.

The interdigitated electrode set can be fabricated on a support, such as a thermally oxidized silicon wafer by photolithography and the lift off technique described in Aoki et al., *Analytical Chemistry*, 62:2206–10 (1990), which is hereby incorporated by reference. See also Aoki et al., *Journal of Electroanalytical Chemistry* 256:259 (1988) and Aoki et al., *Analytical Chemistry* 62:2206–10 (1990), which are also hereby incorporated by reference. Platinum interdigitated electrodes can be formed by several techniques including sputter deposition and the lift-off technique described by Aoki or by thermal evaporation of platinum onto the support. Silver lead patterns, and a platinum electrode and silver reference electrode, if used, are preferably formed by photolithography and the lift-off technique. If possible, all lead wires, preferably composed of silver, should be located distal to the surface of the interdigitated array.

Electrodes as described herein have been fabricated at the Cornell Nanofabrication Facility (Ithaca, N.Y.).

In one embodiment, an electrolyte solution of the test sample and the conjugate (i.e., second binding material/analyte analog/first and second binding material having bound thereto a marker complex including a particle and an electroactive marker) is prepared. Preferably, the conjugate comprises an electroactive marker. The solution is passed through the filtration device, the filtration device is washed, the liposomes are lysed, and the electrochemical detection assembly is placed in contact with the filter membrane of the filtration device. As the electrochemical detection assembly makes contact with the electrolyte solution on the filter membrane, an electrical connection between the first and second conductors is established causing current to flow between the first and second conductors. In particular, a voltage sufficient to induce redox cycling of the electroactive marker is applied across the conductors, causing current to flow between the first and second conductors. The presence or amount of the current is detected and correlated to the presence or amount of the analyte in the test sample.

The electrode set formed on the silicon wafer constitutes an electrochemical detection device (16). The detection device is positioned on the end of an inner stem (4). The inner stem (4) has holes running the length of the body into which two contact wires (2) are inserted, that connect the electrochemical detection device (16) to the voltage source (not shown). The inner housing (8) features an opening for the membrane (18) that allows the electrochemical detection device (16) to be applied directly to the surface of the filtration device (20) after the last wash step has occurred.

In the methods of the present invention, a fixed voltage is applied across the conductors to induce redox cycling of the electroactive marker released from the liposomes captured in the filter membrane. A simple battery can be used to apply the voltage. Other devices which may be used as potentiostats in accordance with the invention include the Cypress (Lawrence, Kans.) System Electrochemical Analyzer (CS-1090) and the BAS (West Lafayette, Ind.) Amperometric Detector (LC-4C, LC-3C, LC-3D).

The solvent for the test sample will normally be an aqueous medium, which may be up to about 40 weight percent of other polar solvents, particularly solvents having from 1 to 6, more usually of from 1 to 4, carbon atoms, including alcohols, dimethylforrnamide and dimethylsulfoxide, dioxane and the like. Usually, the cosolvents will be present in less than about 30–40 weight percent. Under some circumstances, depending on the nature of the sample, some or all of the aqueous medium could be provided by the sample itself.

The pH for the medium will usually be in the range of 4–10, usually 5–9, and preferably in the range of about 6–8. The pH is chosen to maintain a significant level of binding affinity of the binding members and optimal generation of signal by the signal producing system. Various buffers may be used to achieve the desired pH and maintain the pH during the assay. Illustrative buffers include borate, phosphate, carbonate, tris, barbital and the like. The particular buffer employed is usually not critical, but in individual assays, one buffer may be preferred over another. For nucleic acid analytes, it is necessary choose suitable buffers. Such buffers include SSC, sodium chloride, sodium citrate buffer, and SSPE (sodium chloride, sodium phosphate, EDTA).

The concentration of electrolytes in the medium will usually be adjusted to achieve isotonicity or equi-osmolality (or up to about 50 to about 100 mmol/kg hypertonic) with the solution in the interior of the liposomes to prevent their crenation or swelling.

With some increased complexity of the excitation waveform applied by the electroanalyzer, electrochemical measurement in accordance with the invention may also be carried out using stripping voltammetry, employing, for example, liposome encapsulated metal ions for detection and measurement.

Moderate, and desirably substantially constant, temperatures are normally employed for carrying out the assay. The temperatures for the assay and production of a detectable signal will generally be in the range of about 4–65° C., more usually in the range of about 20–38° C., and frequently, will be about 15–45° C.

The concentration, in the liquid sample, of analyte which may be assayed will generally vary from about $10^{-3}$ to about $10^{-20}$M, more usually from about $10^{-5}$ to $10^{-15}$M. Considerations such as the concentration of the analyte of interest and the protocol will normally determine the concentration of the other reagents.

In one embodiment of the present invention, a test device according to the present invention is made by applying a first binding material onto the filter membrane of the filtration device and drying the membrane. Subsequently, the filter membrane is blocked and dried for a suitable time determined by the membrane and blocking agents used, to block the non-specific binding sites on the membrane that might interfere with signal generation and clarity.

In another embodiment of the present invention, the analyte and binding material conjugate or analyte analog conjugate, i.e., the test mixture, are pre-incubated together in the form of a mixture, which may be a solution, suspension, dispersion, or other mixture, prior to application to the filter membrane of the filtration device upon which the first binding material has been immobilized. In a more preferred embodiment, the analyte and binding material conjugate or analyte analog conjugate are pre-incubated at from about 15° C. to about 70° C., preferably, at about 41° C., for up to about 15 minutes before the test mixture is passed through the filtration device. Following application of the test mixture including the analyte and binding material conjugate or analyte analog conjugate, at least one wash buffer is passed through the filtration device to remove any unbound marker material. Subsequently, the washed filter membrane is subjected to a detection process. When appropriate, bound liposomes are lysed prior to detection, either by passing a liposome lysing agent through either the inlet hole or outlet hole of the filtration device, or drying a liposome lysing agent onto the contact surface of the detection device.

In another preferred embodiment of the present invention, the first conjugate, second conjugate, and analyte, i.e., the test mixture, are pre-incubated prior to application to the membrane. In a preferred embodiment, the pre-incubation takes place in solution, at ambient temperatures (but can at temperatures at from about 15° C. to about 70° C.). The tripartite test mixture is then passed through the filtration device, followed by washing of the filter membrane, lysing of liposomes where appropriate, and detection, as described above. In this embodiment, the coupling of the first binding material to a marker complex including a particle and a marker, as well as coupling the second binding material to such a marker complex, increases the amount of signal and therefore the overall sensitivity of the system. The first and second binding materials have the ability to bind more than one analyte molecule, allowing the formation of large-sized aggregates that can be collected on a filter membrane that does not allow large molecular weight molecules to pass through, i.e., a size exclusion membrane. In a preferred embodiment, the filter membrane is nitrocellulose that has been blocked as described above. Marker that is retained on the filter membrane can be detected as described above.

In yet another preferred embodiment of the methods of the present invention, the test mixture further includes a marker conjugate including a third binding material bound to an amplifying marker complex, wherein the amplifying marker complex includes a particle and a marker, and wherein the third binding material is selected to bind with a portion of at least one of the first or second marker complex. In this embodiment, at least one, most preferably, more than one, marker conjugate binds with the first and/or second marker complex, thereby providing an amplified signal. Preferably, the marker of the amplifying marker complex is the same as the marker of the first and/or second marker complex.

For the most part, relatively short times are involved for the use of the test device of the present invention. Usually, the entire assay can be completed within from about 2 to about 20 minutes, often within about 10 to about 15 minutes. In accordance with the present invention, the signal is rapidly, even immediately, detectable.

The use of liposomes as described in the present application provides several advantages over traditional signal production systems employing, for example, enzymes. These advantages include increased signal intensity, shelf stability, and instantaneous release of signal-producing markers, as described in Siebert et al., *Analytica Chimica Acta* 282:297–305 (1993); Yap et al., *Analytical Chemistry* 63:2007 (1991); Plant et al., *Analytical Biochemistry* 176:420–426 (1989); Locascio-Brown et al., *Analytical Chemistry* 62:2587–2593 (1990); and Durst et al., Eds., *Flow Injection Analysis Based on Enzymes or Antibodies*, vol. 14, VCH, Weinheim (1990), each of which is hereby incorporated by reference. For example, initial calculations indicate that the rupture of a single liposome in a typical capillary electrophoresis sample volume would lead to a concentration of 5 $\mu$M $K_4Fe(CN)_6$ at the interdigitated electrode array detector. Therefore, due to the great sensitivity of the interdigitated electrode arrays, the detection of single liposome events should be theoretically possible with the present system.

The test sample may be derived from a wide variety of sources, such as physiologic fluids, illustrated by saliva, sweat, serum, plasma, urine, tear fluid, spinal fluid, etc., chemical processing streams, food, waste water, natural waters, soil extracts, etc. Various addenda may be added to adjust the properties of the test sample, depending upon the properties of the other components of the device, as well as on those of the particle used or the analyte itself. Examples of solution addenda which may be incorporated into test sample include buffers, for example, pH and ionic strength, sample or analyte solubilizing agents, such as, for example, nonpolar solvents, and high molecular weight polymers such as Ficoll®, a nonionic synthetic polymer of sucrose, available from Pharmacia, and dextran.

The conjugate of the first, second, or third binding material and marker complex may be prepared by procedures generally known in the art, with the particular procedure used in a given case being dependent upon the particle components and binding material employed. Such techniques include covalent coupling, derivatization, or activation, and the like. Liposomes may be produced from a component which has been derivatized with the first or second binding material, whereby the liposomes, when produced, are conjugated with the first or second binding material. In another procedure, the liposomes, including the marker, may be initially formed, followed by conjugating the liposomes with the first or second binding material by procedures known in the art.

Liposomes can be prepared from a wide variety of lipids, including phospholipids, glycolipids, steroids, relatively long chain alkyl esters; e.g., alkyl phosphates, fatty acid esters; e.g. lecithin, fatty amines, and the like. A mixture of fatty materials may be employed, such as a combination of neutral steroid, a charge amphiphile, and a phospholipid. Illustrative examples of phospholipids include lecithin, sphingomyelin, and dipalmitoylphosphatidylcholine, etc. Representative steroids include cholesterol, chlorestanol, lanosterol, and the like. Representative charge amphiphilic compounds generally contain from 12 to 30 carbon atoms. Mono- or dialkyl phosphate esters, or alkylamines; e.g. dicetyl phosphate, stearyl amine, hexadecyl amine, dilaurylphosphate, and the like are representative.

The liposome sacs are prepared in aqueous solution containing the marker whereby the sacs will include the marker in their interiors. The liposome sacs may be prepared by vigorous agitation in the solution, followed by removal of the unencapsulated marker. Further details with respect to the preparation of liposomes are set forth in U.S. Pat. No. 4,342,826 and PCT International Publication No. WO 80/01515, both of which are incorporated by reference.

As a matter of convenience, the present device can be provided in a kit in packaged combination with predetermined amounts of reagents for use in assaying for an analyte or a plurality of analytes. Aside from the filtration-detection device, other additives such as ancillary reagents may be included, for example, stabilizers, buffers, and the like. The relative amounts of the various reagents may be varied widely, to provide for concentration in solution of the reagents which substantially optimize the sensitivity of the assay. The reagents can be provided as dry powders, usually lyophilized, including excipients, which on dissolution will provide for a reagent solution having the appropriate concentrations for performing the assay. The kit or package may include other components such as standards of the analyte or analytes (analyte samples having known concentrations of the analyte).

The present invention is applicable to procedures and products for determining a wide variety of analytes. As representative examples of types of analytes, there may be mentioned: environmental and food contaminants, including pesticides and toxic industrial chemicals; drugs, including therapeutic drugs and drugs of abuse; hormones, vitamins, proteins, including enzymes, receptors, and antibodies of all classes; prions; peptides; steroids; bacteria; fungi; viruses; parasites; components or products of bacteria, fungi, viruses, or parasites; aptamers; allergens of all types; products or components of normal or malignant cells; etc. As particular examples, there may be mentioned $T_4$; $T_3$; digoxin; hCG; insulin; theophylline; leutinizing hormones and organisms causing or associated with various disease states, such as streptococcus pyrogenes (group A), Herpes Simplex I and II, cytomegalovirus, chlamydiae, etc. The invention may also be used to determine relative antibody affinities, and for relative nucleic acid hybridization experiments, restriction enzyme assay with nucleic acids, binding of proteins or other material to nucleic acids, and detection of any nucleic acid sequence in any organism, i.e., prokaryotes and eukaryotes.

A filtration-detection device in accordance with the present invention can be used in a variety of assays, such as competitive binding assays and sandwich assays, as described in U.S. Pat. No. 5,789,154 to Durst et al., U.S. Pat. No. 5,756,362 to Durst et al., U.S. Pat. No. 5,753,519 to Durst et al., U.S. Pat. No. 5,958,791 to Roberts et al., U.S. Pat. No. 6,086,324, co-pending U.S. patent application Ser. No. 09/034,086, filed Mar. 3, 1998, co-pending U.S. patent application Ser. No. 09/354,471, filed Jul. 15, 1999, co-pending U.S. patent application Ser. No. 09/315,576, filed May 20, 1999, and co-pending U.S. patent application Ser. No. 09/603,126, filed Jun. 23, 2000, which are hereby incorporated by reference.

As hereinabove indicated, the assay may be qualitative (presence or absence of certain level of analyte) or quantitative or semi-quantitative. The preparation of suitable standards and/or standard curves is deemed to be within the scope of those skilled in the art from the teachings herein.

The method of the invention, and preparation and use of the test device in accordance with the invention, are illustrated by the following Examples.

EXAMPLES

Example 1

Membrane Preparation

Streptavidin was immobilized on nitrocellulose membranes (Predator Membrane, Pall/Gelman, Port Washington, N.Y.). Dots, i.e., immobilization zones, of streptavidin solution (10 pmol/$\mu$L in 0.4 M $Na_2CO_3$/$Na_2HCO_3$ buffer, pH 9.0 containing 5% methanol) were dried on one nitrocellulose membrane (1.5 $\mu$L mixture per dot, equally spaced on membrane) under a fume hood for 5 minutes. Subsequently, they were dried in a vacuum oven (15 psi) at 50° C. for 1.5 hours. The membrane was then soaked in blocking reagent (0.5% polyvinylpyrrolidone, 0.015% casein, in 0.02 M Tris-HCl, 0.15 NaCl buffer, pH 7.0 with 0.01% $NaN_3$) for 30 minutes on a shaker at room temperature. The membrane was blotted dry, placed under the safety hood for 5 minutes and then dried in a vacuum oven (15 psi) at room temperature for 2.5 hours. The membrane was stored in a sealed plastic bag at 4° C.

Membranes were also prepared with both streptavidin and biotinylated oligonucleotide complex (capture probe for *Cryptosporidium parvum*) solution, following the same procedure as described above. Each dot contained 10 pmol/$\mu$L streptavidin and 30 pmol/$\mu$L Bio-CP in 0.4 M $Na_2CO_3$/$NaHCO_3$ buffer, pH 9.0 containing 5% methanol.

Example 2

Preparation of Device

Figure 17:
FIGS. 17A and B show a side view (17A) and top view (17B) of a filter holder with a square piece of nitrocellulose membrane.

A piece of nitrocellulose membrane as described above was placed upon the lower part of a polypropylene filter holder (Osmonics, Minnetonka, Minn.) (FIG. 17) and a syringe was attached to the outlet of the filter holder. The surface area of the filter housing that was not covered by the nitrocellulose membrane was sealed using nail polish.

Example 3

Optical Assay Results

A test solution including a sample and a *C. parvum* reporter probe tagged to sulforhodamine B entrapping liposomes was pipetted onto a nitrocellulose membrane (i.e., filter) with immobilized *C. parvum* capture probes, as described in Example 1, followed by a washing buffer. A synthetic *C. parvum* target sequence was used as the sample for detection, i.e. the more target sequence present, the more intense the signal. Excess solution was drawn out of the filter by a syringe attached to the lower part of the filter.

The signal was analyzed using a computer scanner and determined in gray scale intensities. In all cases shown below, the liposome-target sequence mixture was incubated on the membrane for 4 minutes prior to the application of a washing buffer. The Master mix buffer included 50% formamide, 4×SSC, 0.4 M sucrose, and 0.4% Ficoll type 400. The lipsome-target sequence mixture included 6 $\mu$L Master mix, 1 $\mu$L 16×SSC, 4 $\mu$L liposomes, and 1 $\mu$L target (or water). The washing buffer included 25% formamide, 3×SSC, 0.2 M sucrose, and 0.2% Ficoll type 400.

TABLE 1

Optical Assay Results

| Concentration of Target | Signal (Gray Scale Intensity) | Assay Conditions |
|---|---|---|
| 100 fmol | 11621 | 100 $\mu$L washing buffer |
| 100 fmol | 11261 | 300 $\mu$L washing buffer |
| 100 fmol | 11146 | 100 $\mu$L washing buffer |
| 120 fmol | 16944 | 200 $\mu$L washing buffer |
| 0 fmol | 3673 | 100 $\mu$L washing buffer |
| 0 fmol | 1263 | 300 $\mu$L washing buffer |
| 0 fmol | 5263 | 100 $\mu$L washing buffer |
| 0 fmol | 3007 | 200 $\mu$L washing buffer |

Example 4

Investigation Of Incubation Time

Liposome-target sequence mixtures as described in Example 3 were applied to the nitrocellulose membrane. Prior to applying the washing buffer, the mixture was allowed to stay on the membranes. This "incubation time" was varied from 0–6 minutes and optimized to produce stronger signals without increasing the background signals (i.e. unspecific binding of liposomes to the membrane).

In addition, a pre-incubation time was investigated. Sulforhodamine B-liposomes and the synthetic *C. parvum* target sequence were mixed with the Master mix (see Example 3) and incubated at 41° C. for 0–10 minutes.

Figure 18:
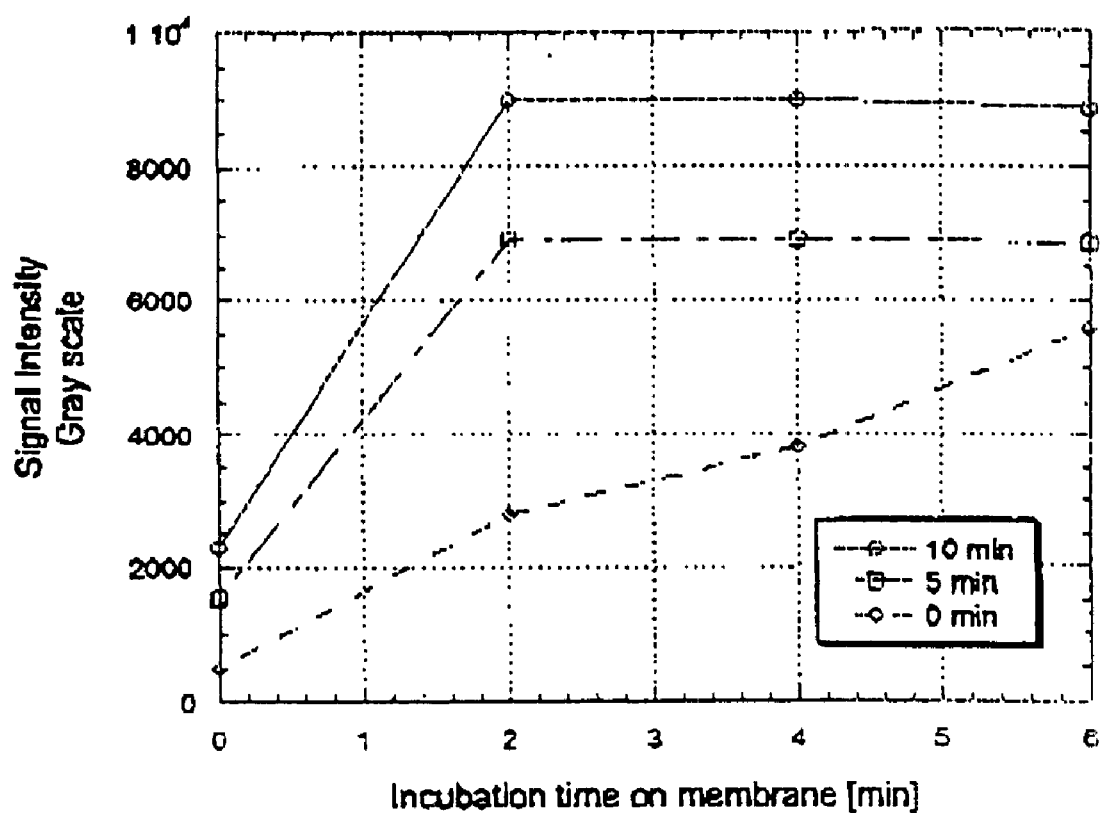
FIG. 18 is a graph showing the variation of pre-incubation time at 41° C. and incubation on a nitrocellulose membrane for detection of 100 fmol target sequence with sulforhodamine B-liposomes in filtration format.

Results of these investigations are summarized in FIG. 18. The results indicate that a 10 minute pre-incubation time at 41° C. plus a incubation for 2 minutes on the membrane is optimal.

Example 5

Electrochemical Assay

Figure 19:
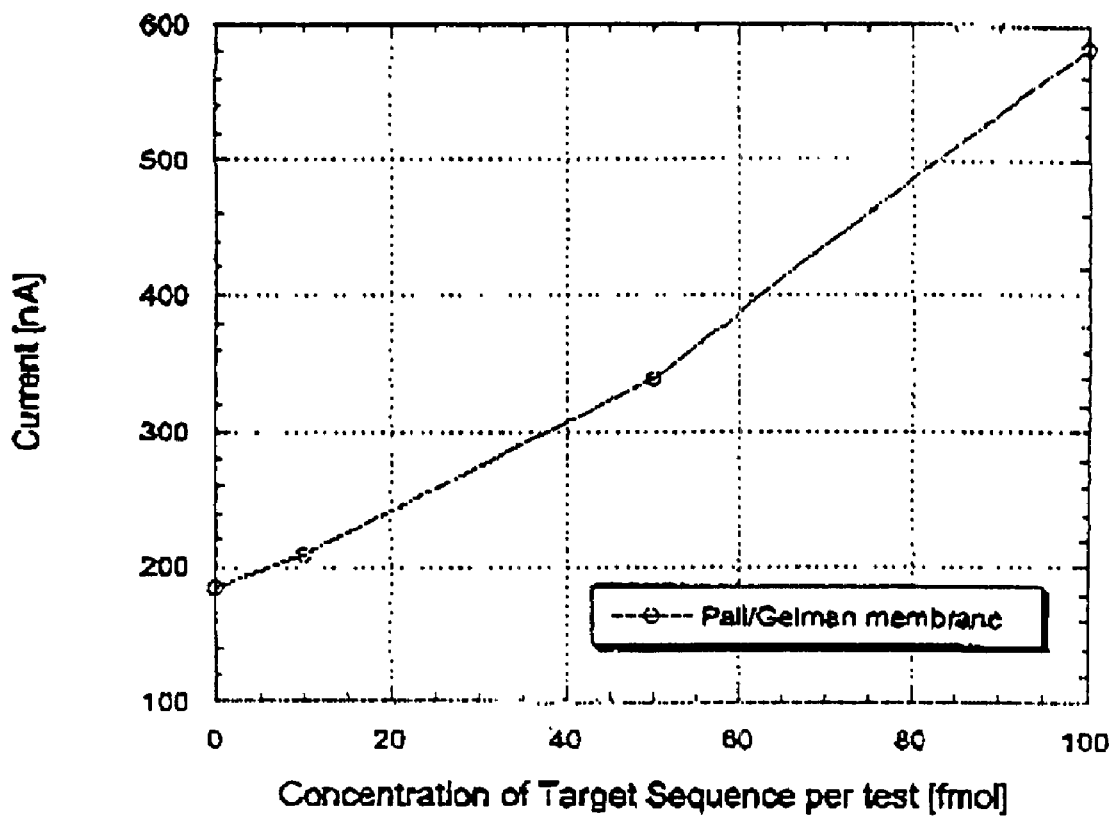
FIG. 19 is a graph showing electrochemical detection of synthetic *C. parvum* target sequence.

Electrochemical liposomes, substituting the electrochemical markers potassium ferro/ferrihexacyanide for sulforhodamine B, the synthetic *C. parvum* target sequence, and Master mix were pre-incubated for 10 minutes at 41° C., and then applied onto a nitrocellulose membrane, as described above. After 2 minutes, 100 $\mu$L of washing buffer was applied to rinse all non-bound liposomes off the membrane. The membrane piece was placed upside down onto an interdigitated ultramicroelectrode array (IDA), 400 mV was applied, and 4 mL of 200 mM detergent solution (octylglucopyranoside (OG)) in 150 mM potassium phosphate buffer (pH 7) was applied to the dry membrane. A signal was reported for 45 seconds to 3 minutes by applying a voltage of 400 mV across the IDA fingers. Signals are summarized in FIG. 19.

Example 6

Comparison Of Membranes

Figure 20:
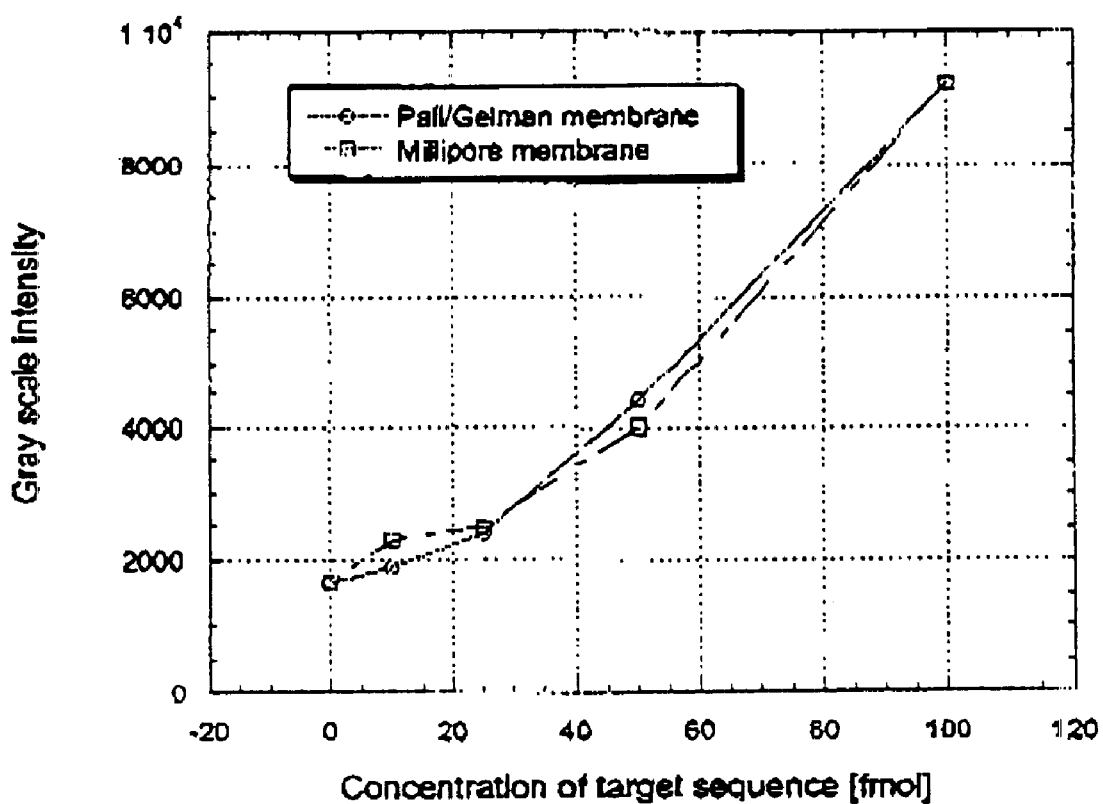
FIG. 20 is a graph showing a comparison of two membranes: Pall/Gelman (Predator) and Millipore (SRHF 00005).

Membranes were obtained from Pall/Gelman (Predator Membrane, Port Washington, N.Y.) and from Millipore (SRHF 00005, roll #53, Bedford, Mass.). Sulforhodamine B-liposomes, the synthetic *C. parvum* target sequence, and Master mix were preincubated for 10 minutes at 41° C. and, subsequently, they were applied onto the membranes. After a 2 minute incubation, 100 µL of washing buffer was applied to rinse all non-bound liposomes off the membranes. Signals were determined using a computer scanner. Signals are summarized in FIG. 20.

Example 7

Nucleic Acid Sequence-Based Amplification (NASBA) Reaction

NASBA was performed using the NucliSens kit from Organon Teknika (The Netherlands) or the RNamplifier from Qiagen (Valencia, Calif.). Five µL of sample was mixed with 10 µL NASBA reaction mixture and incubated for 5 minutes at 65° C. and then for 5 minutes at 41° C. Five µL of NASBA enzyme cocktail was added and the mixture incubated for another 60–90 minutes at 41° C. The NASBA amplicon was used directly for detection of stored sample at −20° C.

What is claimed:

1. A filtration-detection device for detecting or quantifying an analyte in a test sample comprising:
   a filtration device comprising a porous membrane having a first binding material immobilized thereto, wherein the porous membrane is supported on a support having an opening for passage of the test sample away from the porous membrane, and wherein the first binding material binds to a portion of the analyte; and
   a detection assembly movable between a first position out of contact with the filtration device and a second position in electrolytic contact with the filtration device to detect or quantify analyte bound to the first binding material.

2. A device according to claim 1, wherein said detection assembly is in contact with the filtration device.

3. A device according to claim 1, wherein said filtration device comprises a nitrocellulose membrane.

4. A device according to claim 1, wherein said first binding material is selected from the group consisting of an antibody, an antigen, a nucleic acid sequence, an aptamer, and a cell receptor.

5. A device according to claim 1, wherein said analyte is a target nucleic acid molecule and said first binding material is a capture probe selected to hybridize with a portion of said target nucleic acid molecule.

6. A device according to claim 5, wherein said target nucleic acid molecule is found in an organism selected from the group consisting of bacteria, fungi, viruses, protozoa, parasites, animals, and plants.

7. A device according to claim 6, wherein said organism is *Cryptosporidium parvum*.

8. A device according to claim 1, wherein said detection assembly is an electrochemical detection assembly.

9. A device according to claim 8, wherein said electrochemical detection assembly comprises an electrode array comprising a first conductor having a plurality of fingers and a second conductor having a plurality of fingers, wherein said fingers of said first conductor are interdigitated with said fingers of said second conductor, said first and second conductors are electrically connected to one another via a voltage source and readout device, and said array is positioned to induce redox cycling of an electroactive marker.

10. A device according to claim 9, wherein said device further comprises a reference electrode electrically connected to said electrode array.

11. A device according to claim 9, wherein either or both of said first conductor and said second conductor comprise one or more materials selected from the group consisting of platinum, gold, graphite, and silver.

12. A device according to claim 9, wherein each of said first conductor and said second conductor comprise from 2 to 1000 fingers.

13. A device according to claim 9, wherein said fingers of each of said first conductor and said second conductor are from about 1 µm to about 20 µm wide and are spaced from about 1 nm to about 10 µm apart.

14. A device according to claim 9, wherein each of said first conductor and said second conductor further comprises a contact pad through which the fingers are electrically connected to the voltage source, and wherein said contact pad is at least partially coated with an insulating material.

15. A device according to claim 1, wherein said detection assembly is an optical detection assembly.

* * * * *

UNITED STATES PATENT AND TRADEMARK OFFICE
CERTIFICATE OF CORRECTION

PATENT NO. : 6,576,460 B1
DATED : June 10, 2003
INVENTOR(S) : Baeumner et al.

It is certified that error appears in the above-identified patent and that said Letters Patent is hereby corrected as shown below:

Title page,
Item [75], Inventors, "Antje J. Baeumner, Ithaca, NY (US); Richard A. Montagna, Grand Island, NY (US)" should be -- Antje J. Baeumner, Ithaca, NY (US) --.
Item [73], Assignees, "Cornell Research Foundation ,Inc., Ithaca, NY (US); Innovative Biotechnologies International, Inc., Grand Island, NY (US)" should be -- Cornell Research Foundation, Inc., Ithaca, NY (US) --.

Signed and Sealed this

Sixth Day of July, 2004

JON W. DUDAS
*Acting Director of the United States Patent and Trademark Office*